US012279863B2

(12) United States Patent
Althobaiti et al.

(10) Patent No.: US 12,279,863 B2
(45) Date of Patent: Apr. 22, 2025

(54) NON-INVASIVE SENSOR AND METHOD FOR DETERMINING BLOOD GLUCOSE

(71) Applicant: Imam Abdulrahman Bin Faisal University, Dammam (SA)

(72) Inventors: Murad Mohsen Althobaiti, Dammam (SA); Ibraheem Al-Naib, Dammam (SA)

(73) Assignee: Imam Abdulrahman Bin Faisal University, Dammam (SA)

( * ) Notice: Subject to any disclaimer, the term of this patent is extended or adjusted under 35 U.S.C. 154(b) by 742 days.

(21) Appl. No.: 17/553,181

(22) Filed: Dec. 16, 2021

(65) Prior Publication Data

US 2023/0190143 A1 Jun. 22, 2023

(51) Int. Cl.
*A61B 5/145* (2006.01)
*A61B 5/00* (2006.01)

(52) U.S. Cl.
CPC ........ *A61B 5/14532* (2013.01); *A61B 5/0075* (2013.01); *A61B 5/6816* (2013.01); *A61B 5/6826* (2013.01); *A61B 5/742* (2013.01)

(58) Field of Classification Search
CPC . A61B 5/14532; A61B 5/0075; A61B 5/1455; A61B 5/0071; A61B 5/0095; A61B 5/6816; A61B 5/6826; A61B 5/681; A61B 5/6825; G01N 21/35; G01N 21/359
See application file for complete search history.

(56) References Cited

U.S. PATENT DOCUMENTS

| 6,016,435 | A | * | 1/2000 | Maruo | A61B 5/14532 |
| | | | | | 600/316 |
| 2016/0091496 | A1 | | 3/2016 | Xu et al. | |
| 2017/0105663 | A1 | * | 4/2017 | Dhawan | A61B 5/14546 |
| 2017/0319131 | A1 | | 11/2017 | Xavier Da Silveira et al. | |
| 2018/0085040 | A1 | * | 3/2018 | Ferber | A61B 5/0205 |
| 2020/0337606 | A1 | * | 10/2020 | Hazen | A61B 5/6824 |

OTHER PUBLICATIONS

Yadav, et al. ; Levenberg-Marquardt-based non-invasive blood glucose measurement system ; IETE Journal of Research ; Aug. 23, 2017 ; 9 Pages.

* cited by examiner

*Primary Examiner* — Eric F Winakur
*Assistant Examiner* — Sienna C Pyle
(74) *Attorney, Agent, or Firm* — Oblon, McClelland, Maier & Neustadt, L.L.P.

(57) ABSTRACT

A non-invasive glucose sensor used for glucose detection in a subject is provided. The sensor includes a long channel source to excite a first location of a skin and a long channel detector to detect near infrared (NIR) energy emitted from the first location of the skin. A short channel source excites a second location of the skin and a short channel detector detects NIR energy emitted from the second location of the skin. The sensor further includes a long channel processor to process a long channel electrical signal into a glucose spectroscopic data and a short channel processor to process a short channel electrical signal into a background spectroscopic data. The sensor includes a spectroscopic processor to subtract the background spectroscopic data from the glucose spectroscopic data, and thereby to produce data indicative of a quantity of glucose present in the subject's blood.

16 Claims, 10 Drawing Sheets

NON-INVASIVE SENSOR AND METHOD FOR DETERMINING BLOOD GLUCOSE

STATEMENT REGARDING PRIOR DISCLOSURE BY THE INVENTORS

Aspects of this technology are described in an article titled "Optimization of Dual-Channel Near-Infrared Non-Invasive Glucose Level Measurement Sensors Based On Monte-Carlo Simulations" published in IEEE Photonics Journal, Vol. 13, No. 3, June 2021, on May 14, 2021, which is incorporated herein by reference in its entirety.

BACKGROUND OF THE INVENTION

Technical Field

The present disclosure is directed to a sensor, and particularly, to a non-invasive glucose sensor and a method for determining glucose levels in a subject's blood.

Description of Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Biosensors are analytical devices used to detect and analyze biochemical substances. Biosensors measure biological or chemical reactions by generating signals proportional to the concentration of an analyte in the reaction. For example, there are biosensors for diabetes management that analyze the glucose content of the blood and report the current status of metabolism.

Conventional biosensors employ techniques based on advanced electrochemical reactions to estimate glucose levels in the blood [J. Diabetes Sci. Technol, 2009, 3, 5, 1207-1214, incorporated by reference herein in its entirety]. However, electrochemical sensors tend to have a limited lifetime and low accuracy, and are not user-friendly [RSC Adv, 2013, 3, 14, incorporated by reference herein in its entirety]; [Chem. Rev, 2008, 108, 2, incorporated by reference herein in its entirety].

Continuous Glucose Monitoring Sensors (CGMS) are currently available in the market [Sensors J, 2019, 19, 2, 535-547, incorporated by reference herein in its entirety]; [Diabetes. Metab. Res. Rev, 2020, 36, 8, incorporated by reference herein in its entirety]. CGMS can estimate blood glucose levels every 1-5 minutes. CGMS typically contains a small filament inserted beneath the skin and measures glucose based on an enzymatic reaction. However, due to the immune response of the body and degradation of reagents, CGMS must be replaced regularly [Int. J. Pharm, 2018, 544, 2, 319-334, incorporated by reference herein in its entirety]. Additional disadvantages of these sensors include the short lifetimes and the need for daily calibration.

Conventional non-invasive glucose monitoring sensors have been considered as potential alternatives to address the issues involving the current CGMS [Analytica Chimica Acta, 2012, 750, incorporated by reference herein in its entirety]; [Clin. Biochem, 2009, 42, 3, incorporated by reference herein in its entirety]. Non-invasive glucose monitoring sensors are still in the development stage. Only a couple of non-invasive sensors, based on reverse iontophoresis and impedance spectroscopy, are commercially available [J. Electroanal. Chem, 2011, 660, 1, incorporated by reference herein in its entirety]; [Diabetes. Metab. Res. Rev, 2002, 18, 1, incorporated by reference herein in its entirety]; [Biosens. Bioelectron, 2003, 19, 3, incorporated by reference herein in its entirety]. These non-invasive glucose monitoring sensors have faced clinical challenges such as skin irritations caused by the GlucoWatch. Additionally, the conventional non-invasive glucose monitoring sensors suffer from low accuracy. In fact, the conventional non-invasive glucose monitoring sensors were briefly discontinued after initial release, due to their low accuracy, user discomfort, and high cost [Diabetologia, 2005, 48, 6, incorporated by reference herein in its entirety], [Diabetes Care, 2004, 27, 3, incorporated by reference herein in its entirety].

In the field of Near-Infrared (NIR) spectroscopy, many techniques have been extensively investigated in an attempt to noninvasively measure the glucose level in the blood. The short wavelength band of the NIR spectrum was evaluated for finger spectra measurements [Clin. Chem, 1992, 38, 9, incorporated by reference herein in its entirety], [Int. J. Artif. Organs, 1997, 20, 5, incorporated by reference herein in its entirety]. Recently, researchers investigated the correlation between dermal interstitial fluid glucose and plasma glucose [J. Lab. Clin. Med, 1997, 130, 4, 436-441, incorporated by reference herein in its entirety], [Sensors 2021, 21, 6820, incorporated by reference herein in its entirety], [Anal. Bioanal. Chem., vol. 411, pp. 63-77, January 2019, incorporated by reference herein in its entirety], [IEEE Photon. J, vol. 8, no. 6, December 2016, Art. no. 6805911, incorporated by reference herein in its entirety]. They found that there is no significant difference between measuring glucose levels from dermal glucose and plasma glucose. Epidermis degrades the total signal received by a detector by adding an interference noise to the measured signal. Hence, such sensors fail to provide accurate data on blood glucose levels [Diabetes Technol. Ther, 2001, 3, 3, 357-365, incorporated by reference herein in its entirety].

In view of the foregoing, there is still a need to develop label-free, compact, user-friendly, and inexpensive non-invasive biosensors which are capable of providing an accurate and efficient measurement of blood glucose.

SUMMARY

In an exemplary embodiment, a non-invasive glucose sensor for a subject is described. The non-invasive glucose sensor includes a long channel source that excites the first location of the skin of the subject with a first near-infrared (NIR) energy of 1700-1800 nanometer (nm). The non-invasive glucose sensor further includes a long channel detector that detects NIR energy emitted from the first location of the skin upon excitation of the first NIR energy. The non-invasive glucose sensor further includes a short channel source that excites a second location of the skin of the subject with a second NIR energy of 1400-1500 nm. The non-invasive glucose sensor further includes a short channel detector that detects NIR energy emitted from the second location of the skin upon excitation of the second NIR energy. The non-invasive glucose sensor further includes a long channel processor that processes a long channel electrical signal produced by the long channel detector into glucose spectroscopic data. The non-invasive glucose sensor further includes a short channel processor that processes a short channel electrical signal produced by the short channel detector into background spectroscopic data. The non-invasive glucose sensor further includes a spectroscopic processor that subtracts the background spectroscopic data from the glucose spectroscopic data, thereby producing data indicative of a quantity of glucose present in the subject's blood. The first and the second locations of the skin are each adjacent to an external epidermis of the skin.

In some embodiments, the first NIR energy has a wavelength of about 1750 nm.

In some embodiments, the second NIR energy has a wavelength of about 1450 nm.

In some embodiments, a source-detector distance between the long channel source and the long channel detector is from 5 to 7 millimeters (mm).

In some embodiments, the source-detector distance between the long channel source and the long channel detector is about 6 mm.

In some embodiments, a source-detector distance between the short channel source and the short channel detector is from 1 to 3 mm.

In some embodiments, the source-detector distance between the short channel source and the short channel detector is about 2 mm.

In some embodiments, the non-invasive glucose sensor includes a long channel source guide that directs the first NIR energy to the first location of the skin of the subject, and a long channel detector guide that directs the NIR energy emitted from the first location of the skin upon excitation of the first NIR energy to the long channel detector.

In some embodiments, the non-invasive glucose sensor includes a short channel source guide that directs the second NIR energy to the second location of the skin of the subject, and a short channel detector guide that directs the NIR energy emitted from the second location of the skin upon excitation of the second NIR energy to the short channel detector.

In some embodiments, the long channel source and the short channel source each independently include at least one light source that emits 1 million to 100 million photons.

In some embodiments, the long channel detector and the short channel detector each independently include at least one photodiode.

In some embodiments, the long channel source guide, the long channel detector guide, the short channel source guide, and the short channel detector guide each independently include at least one optical fiber.

In some embodiments, the distance between the first and the second locations of the skin is about 8-12 mm.

In some embodiments, the subject is a human.

In some embodiments, the skin is located on the hands, forearms, forehead, face, fingers, and/or earlobes of the subject.

In another exemplary embodiment, a wearable electronic device is described. The wearable electronic device includes the non-invasive glucose sensor and an electronic arrangement for performing a standard function of the wearable electronic device.

In yet another exemplary embodiment, a method of determining glucose level in a subject's blood using the non-invasive glucose sensor is described. The method includes exciting a first location of the skin of the subject with the first NIR energy using the long channel source. The method further includes detecting NIR energy emitted from the first location of the skin using the long channel detector. The method further includes processing a long channel electrical signal produced by the long channel detector into glucose spectroscopic data using the long channel processor. The method further includes exciting a second location of the skin of the subject with the second NIR energy using the short channel source. The method further includes detecting NIR energy emitted from the second location of the skin using the short channel detector. The method further includes processing a short channel electrical signal produced by the short channel detector into background spectroscopic data using the short channel processor. The method further includes subtracting the background spectroscopic data from the glucose spectroscopic data using the spectroscopic processor, thereby producing data indicative of a quantity of glucose present in the subject's blood.

In some embodiments, the first NIR energy has a wavelength of about 1750 nm, the second NIR energy has a wavelength of about 1450 nm, a source-detector distance between the long channel source and the long channel detector is about 6 mm, and a source-detector distance between the short channel source and the short channel detector is about 2 mm.

In some embodiments, the quantity of glucose is determined using absorption signals ranging from 1200 nm to 1900 nm of the data produced by subtracting the background spectroscopic data from the glucose spectroscopic data using the spectroscopic processor.

In some embodiments, the glucose spectroscopic data has a dermis sensitivity of about 40%, and the background spectroscopic data has an epidermis sensitivity of about 30%.

The foregoing general description of the illustrative present disclosure and the following detailed description thereof are merely exemplary aspects of the teachings of this disclosure and are not restrictive.

BRIEF DESCRIPTION OF THE DRAWINGS

A more complete appreciation of this disclosure and many of the attendant advantages thereof will be readily obtained as the same becomes better understood by reference to the following detailed description when considered in connection with the accompanying drawings, wherein.

DETAILED DESCRIPTION

In the drawings, like reference numerals designate identical or corresponding parts throughout the several views. Further, as used herein, the words "a," "an" and the like generally carry the meaning of "one or more," unless stated otherwise. Within the description of this disclosure, where a numerical limit or range is stated, the endpoints are included unless stated otherwise. Also, all values and subranges within a numerical limit or range are specifically included as if explicitly written out.

As used herein, the terms "approximately," "approximate," "about," and the like may be used when describing magnitude and/or position to indicate that the value and/or position described is within a reasonable range of values and/or positions. For example, a numeric value may have a value that is +/±0.1% of the stated value (or range of values), +/±1% of the stated value (or range of values), +/±2% of the stated value (or range of values), +/±5% of the stated value (or range of values), +/±10% of the stated value (or range of values), or +/±15% of the stated value (or range of values).

Aspects of this disclosure are directed to a non-invasive glucose sensor having at least two sources and corresponding detectors to emit and receive near-infrared radiations (NIR) to quantitatively analyze the amount of blood glucose level. The non-invasive glucose sensor includes a plurality of processors to process and analyze data obtained through NIR spectroscopy. The non-invasive glucose sensor may excite different or similar portions of the skin of a subject allowing passage of NIR radiations from different layers of the skin.

The sources (i.e., light sources) of the non-invasive glucose sensor are configured to provide NIR optical radiations at different wavelengths, for example, at a wavelength ranging from 800 to 2500 nm, from 1000 to 2000 nm, or from 1400 to 1800 nm. Each source (e.g., the long channel source, the short channel source) may include one or more light sources that are configured as a point optical source. The sources may be operated in a manner that allows for the measurement of a blood constituent or analyte, such as blood glucose. Preferably, the non-invasive glucose sensor includes at least one long-channel source that excites at a first location of the skin of the subject with a first NIR energy of 1700-1800 nm, preferably of about 1750 nm, and at least one short-channel source that excites a second location of the skin of the subject with a second NIR energy of 1400-1500 nm, preferably of about 1450 nm.

Exemplary light sources that may be used independently as the long channel and short channel sources for NIR excitations include, but are not limited to, near-infrared LED light, and near-infrared Radiation Organic Light Emitting Diode (NIR-OLED).

The detectors of the non-invasive glucose sensor are configured to detect optical radiations from the sources after attenuation by the tissue (e.g., skin) at different measurement locations, and each output a respective electrical signal responsive to the detected optical radiation. The detectors are operable to detect NIR energies emitted from different locations. In some embodiments, the detectors are operable to receive the reflection and/or transmission portion of the emitted NIR energies. Preferably, the detectors are operable to receive only the reflection portion of the emitted NIR energies.

The detectors may be each configured to output a respective electrical signal responsive to the detected optical radiation. Specifically, the non-invasive glucose sensor includes at least one long channel detector that detects NIR energy emitted from the first location of the skin upon excitation of the first NIR energy and at least one short channel detector that detects NIR energy emitted from the second location of the skin upon excitation of the second NIR energy.

In preferred embodiments, the detectors of the currently disclosed glucose sensor include at least one photodiode, such as a PN photodiode, a p-i-n photodiode, an avalanche photodiode, or a Schottky photodiode. Non-limiting examples of photodiodes include a silicon-based photodiode, an InGaAs-based photodiode, an InPGaAs based photodiode, a PBS-based photodiode, or a PbSe based photodiode.

As used herein, a distance between a light source and a corresponding detector is termed as "source-detector distance." In general, the absolute value of the intensity of the reflection and/or transmission portion of the emitted energy increases as the source-detector distance decreases, i.e., detecting at a location closer to the light source.

As described below, a more effective blood glucose measurement has been achieved through selections of specific excitation wavelengths of the dual-channel sources (i.e., the long and short channel sources) and source-detector distances of the dual-channel. In particular, a synergistic effect, including effective noise interference suppression of the epidermis layer and glucose signal enhancement of the dermis layer, has been realized when (i) the first NIR energy of the long channel source has a wavelength of 1700-1800 nm, preferably about 1750 nm, (ii) the second NIR energy of the short channel source has a wavelength of 1400-1500 nm, preferably about 1450 nm, (iii) a source-detector distance between the long channel source and the detector is 5-7 mm, preferably about 6 mm, and (iv) a source-detector distance between the short channel source and the detector is 1-3 mm, preferably about 2 mm.

The non-invasive glucose sensor disclosed herein may be used for detecting the quantity of glucose present in a subject's blood. In most embodiments, the subject is a mammal, including but not limited to a human, a non-human primate such as a chimpanzee, domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

The non-invasive glucose sensor may be particularly useful for monitoring blood glucose levels in subjects with diabetes or subjects with prediabetes. Prediabetic subjects have a blood glucose level higher than normal but not high enough to be diabetic. For example, prediabetes subjects may have a level of hemoglobin A1c between 5.7-6.4% and/or a fasting blood glucose level of 100-125 mg/dl. Diabetes may be a polygenic form of diabetes (e.g., type 1 diabetes, type 2 diabetes), a monogenic form of diabetes (e.g., neonatal diabetes mellitus, maturity-onset diabetes of the young), or cystic fibrosis-related diabetes. The term "polygenic" refers to the risk of developing these forms of diabetes is related to multiple genes. The term "monogenic" refers to rare forms of diabetes that result from mutations in a single gene.

The non-invasive glucose sensor disclosed herein uses near-infrared (NIR) radiation to measure the blood glucose level. Accordingly, the non-invasive glucose sensor 100 measures blood glucose levels without the need to draw blood or puncture the skin, which often causes pain or trauma.

Figure 1:
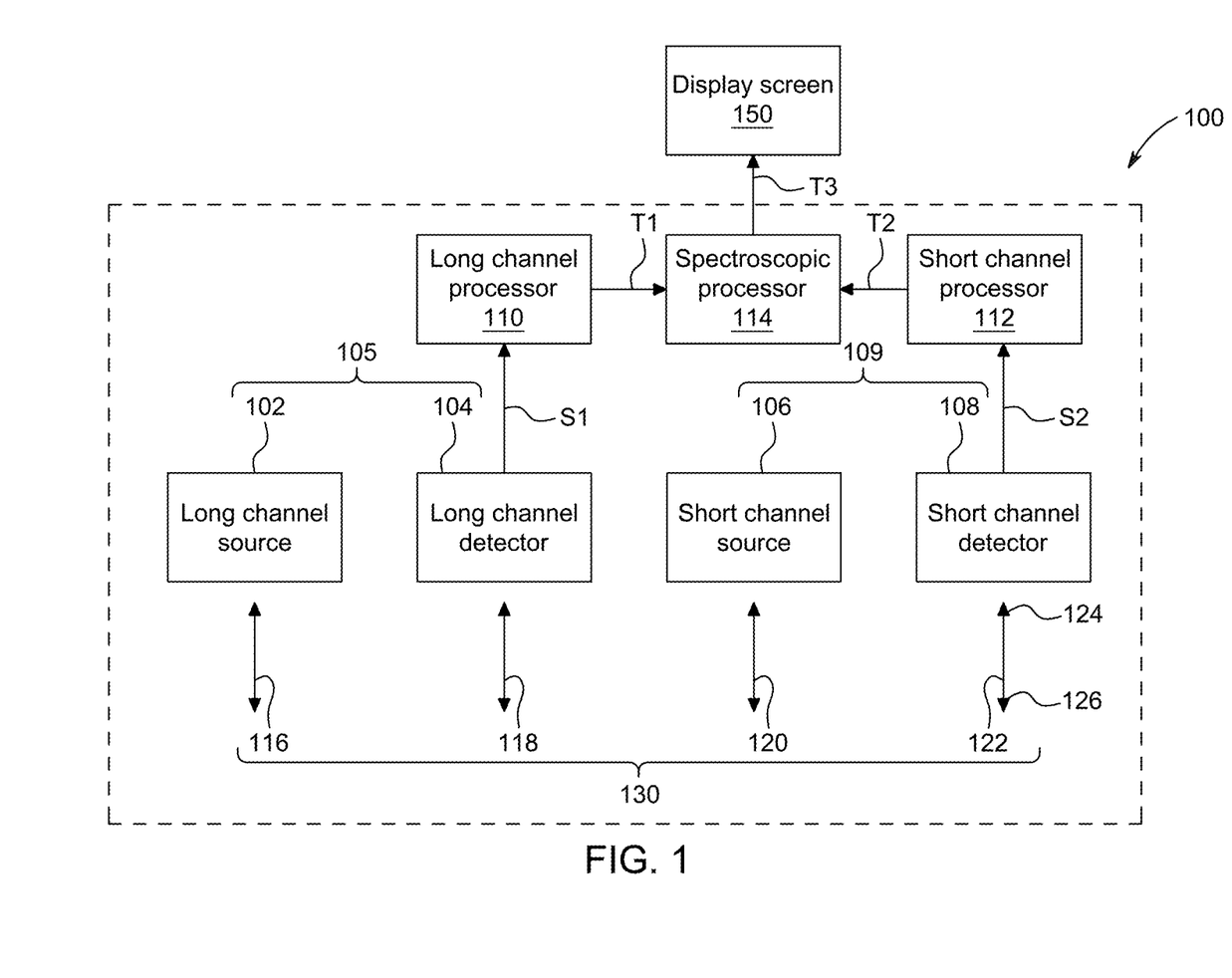
FIG. 1 is a schematic block diagram of a non-invasive glucose sensor for detecting glucose levels in a subject's blood, according to certain embodiments.

Referring to FIG. 1, a schematic block diagram of a non-invasive glucose sensor 100 is illustrated. The non-invasive glucose sensor 100 includes a long channel source 102 and a short channel source 106. The long channel source 102 and the short channel source 106 each independently include at least one light source that emits 1 million to 100 million photons. The light source may emit from about 2 million to 90 million photons, preferably from about 5 million to 80 million, preferably from about 10 million to 75 million, preferably from about 25 million to 70 million, preferably from about 50 million to 60 million photons.

The non-invasive glucose sensor 100 includes a long channel detector 104 and a short channel detector 108. The long channel detector 104 and the short channel detector 108 each independently include at least one photodiode.

The long channel source 102 and the long channel detector 104 are collectively referred to as 'the long channel devices 105'. The short channel source 106 and the short channel detector 108 are collectively referred to as 'the short channel devices 109'. In one embodiment, the long and short channel devices 105, 109 may work on the same time. In an alternative embodiment, the long and short channel devices 105 and 109 may work on different times having a difference of between nanoseconds to milliseconds.

The non-invasive glucose sensor 100 uses a dual-channel approach including the long and short channel devices 105, 109. The long and short channel devices 105, 109 may each independently include at least one optode. In some embodiments, the long channel and short channel sources 102, 106 and the long channel and short channel detectors 104, 108 may include optical filters which allow passage of only monochromatic NIR. In some embodiments, the long channel and short channel sources 102, 106 and the long channel and short channel detectors 104, 108 may be in the form of pencils and discs, respectively.

The non-invasive glucose sensor 100 further includes a long channel processor 110, a short channel processor 112 and a spectroscopic processor 114. In one embodiment, the long channel processor 110, the short channel processor 112, and the spectroscopic processor 114 are included within the non-invasive glucose sensor 100. In an alternative embodiment, the long channel processor 110, the short channel processor 112, and the spectroscopic processor 114 may collectively or individually form a separate unit and configured to communicate with the long channel and the short channel detectors 104, 108 of the non-invasive glucose sensor 100.

Figure 2A:
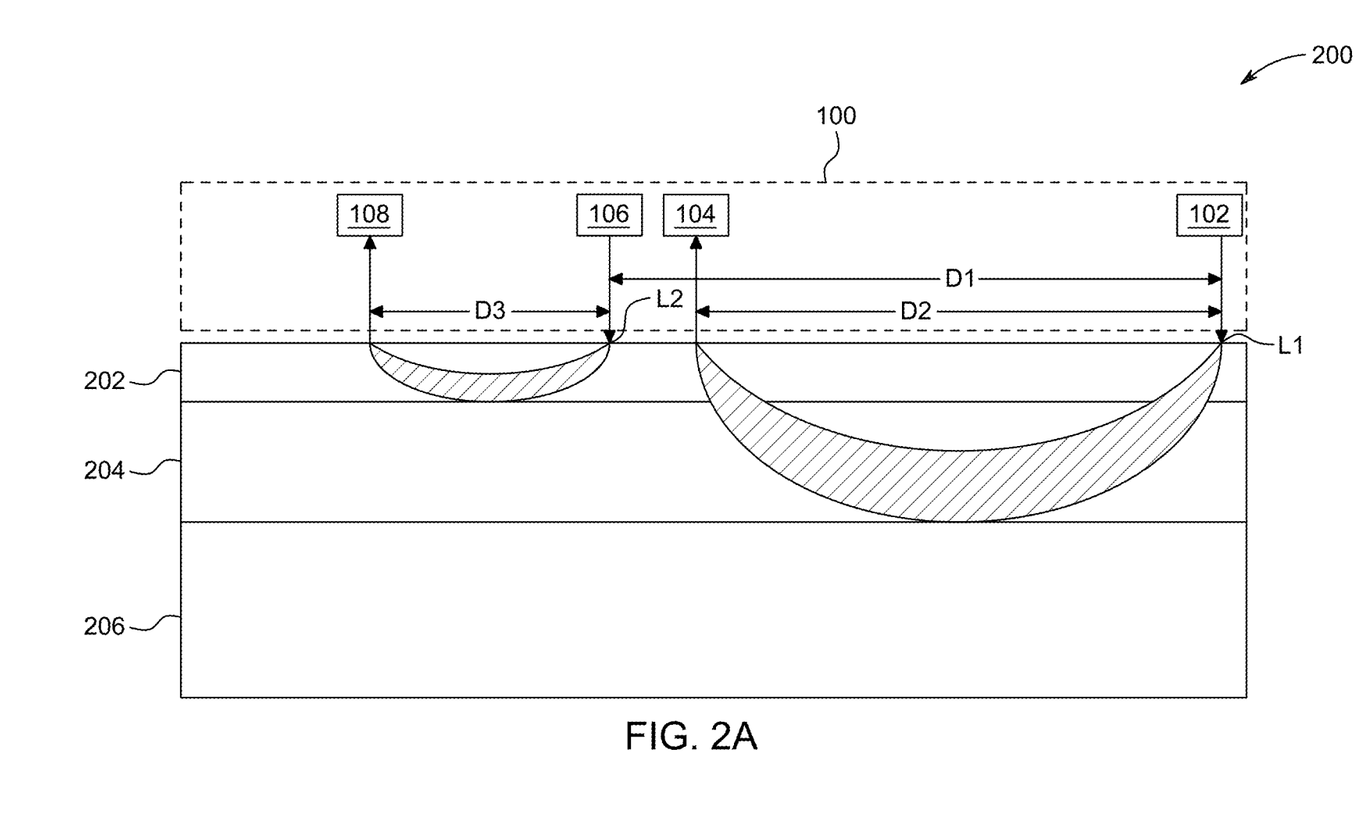
FIG. 2A is a schematic representation showing the non-invasive glucose sensor of FIG. 1 in contact with the skin of the subject, according to certain embodiments.

The non-invasive glucose sensor 100 further includes a long channel source guide 116, a long channel detector guide 118, a short channel source guide 120, and a short channel detector guide 122, which are collectively referred to as 'the guides 130' and individually referred to as 'the guide 130' unless otherwise specifically noted. The long channel source guide 116, the long channel detector guide 118, the short channel source guide 120, and the short channel detector guide 122 each independently includes at least one optical fiber. The number of optical fibers may vary depending upon the arrangement of other components of the non-invasive glucose sensor 100. Each of the guides 130 includes a first end 124 and a second end 126. The first end 124 of each of the guides 130 is connected to the long and short channel devices 105, 109. The second end 126 of each of the guides 130 emits or receives NIR radiations on a skin 200 (shown in FIG. 2) of the subject. In some embodiments, the second end 126 of the guides 130 may or may not be in contact with a surface of the skin 200.

Another aspect of the present disclosure relates to a wearable electronic device that includes the non-invasive glucose sensor of the previous aspect, and an electronic arrangement for performing a standard function of the wearable electronic device.

The non-invasive glucose sensor can take on a variety of predetermined shapes, such as flat rhombohedral, spherical, and toric, among others. In a preferred embodiment, the non-invasive glucose sensor has a toric shape. The toric shape defines the contact surface which is applied to skin to ensure good contact and light communication between the light source and skin, and the detector and skin. When installed on a wearable device, a long axis of the toric shape corresponds with a circumference of the appendage to which the non-invasive glucose sensor is attached. The toric shape provides advantages with regard to maintaining steady contact at a particular skin measurement location (e.g., the first/second locations of the skin). Additionally, the long axis of the toric shape is coincident and/or parallel with the circumference of the appendage on which the glucose sensor is mounted. This feature ensures that the glucose sensor does not migrate along the circumference of the appendage. The toric shape exerts a lateral pressure on the skin, preventing migration along the circumference and keeping the glucose sensor in position.

Figure 8:
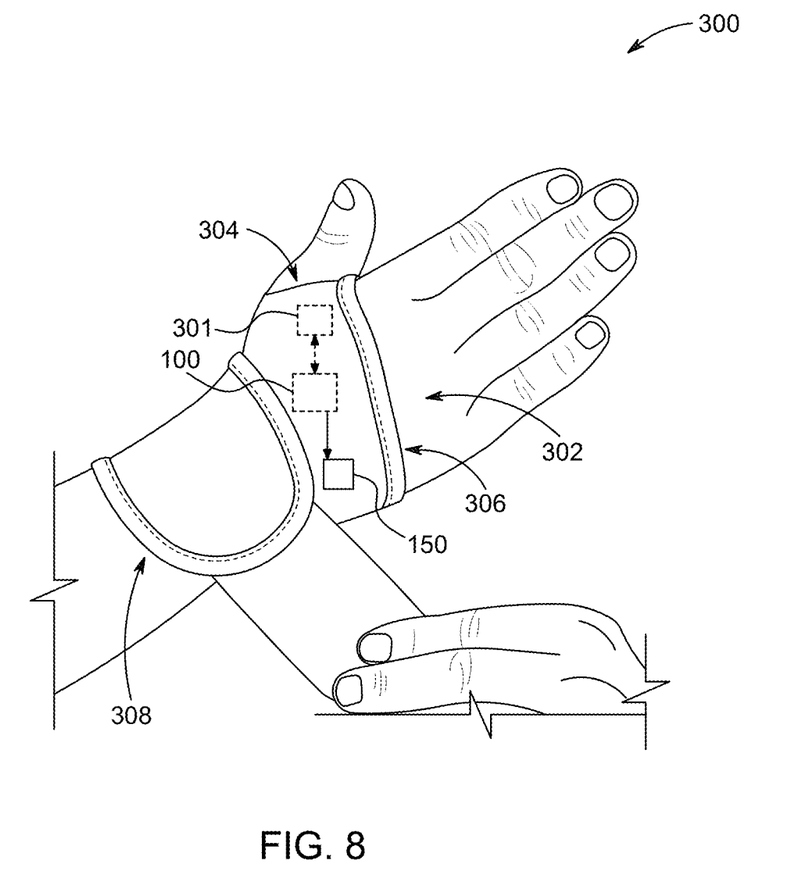
FIG. 8 is a schematic perspective view of a wearable electronic device having the non-invasive glucose sensor of FIG. 1, according to certain embodiments.

Referring to FIG. 8, a schematic perspective view of a wearable electronic device 300 is illustrated. The wearable electronic device 300 includes the non-invasive glucose sensor 100 and an electronic arrangement 301 for performing a standard function of the wearable electronic device 300. The electronic arrangement 301 includes a plurality of wires for connecting different components of the non-invasive glucose sensor 100 together. The electronic arrangement 301 may act as a control unit for controlling operation of the non-invasive glucose sensor 100. The wearable electronic device 300 includes a first support 302 having a first opening 304 configured to receive a thumb of the hand of the subject therethrough and a second opening 306 wider than the first opening 304 configured to receive fingers therethrough, and a second support 308. The first support 302 includes an outer surface and an inner surface. The inner surface touches the skin 200 of the hand.

In the present embodiment, the non-invasive glucose sensor 100 and the electronic arrangement 301 are embedded within the inner and outer surfaces of the first support 302 of the wearable electronic device 300. In some embodiments, a portion of the non-invasive glucose sensor 100 may emerge outside the inner surface of the wearable electronic device 300. In an alternative embodiment, the non-invasive glucose sensor 100 may be just glued to the inner surface of the wearable electronic device 300. In an alternative embodiment, a plurality of holes may be made over the inner surface of the wearable electronic device 300 to allow the long channel and short channel sources 102, 106 and the long channel and short channel detectors 104, 108 to come in contact with the skin 200.

The second support 308 is fitted to wrist of the hand through a hook and loop fastener such as a Velcro coupling. In the present embodiment, the display screen 150 may be coupled to the outer surface of the wearable electronic device 300. The display screen 150 highlights the quantity of glucose present in the subject's blood. In some embodiments, the quantity of glucose may be displayed to a smartphone of user, as the smartphone may be connected to the wearable electronic device 300 via Bluetooth or Wireless Fidelity (Wi-Fi). In some embodiments, the wearable electronic device 300 may be a smart watch, a clip like structure holding a portion of the skin 200 in between, a footwear, a calf band, a bangle and the like. Further, the wearable electronic device 300 may be used to detect blood glucose level at any time during a day.

Figure 2B:
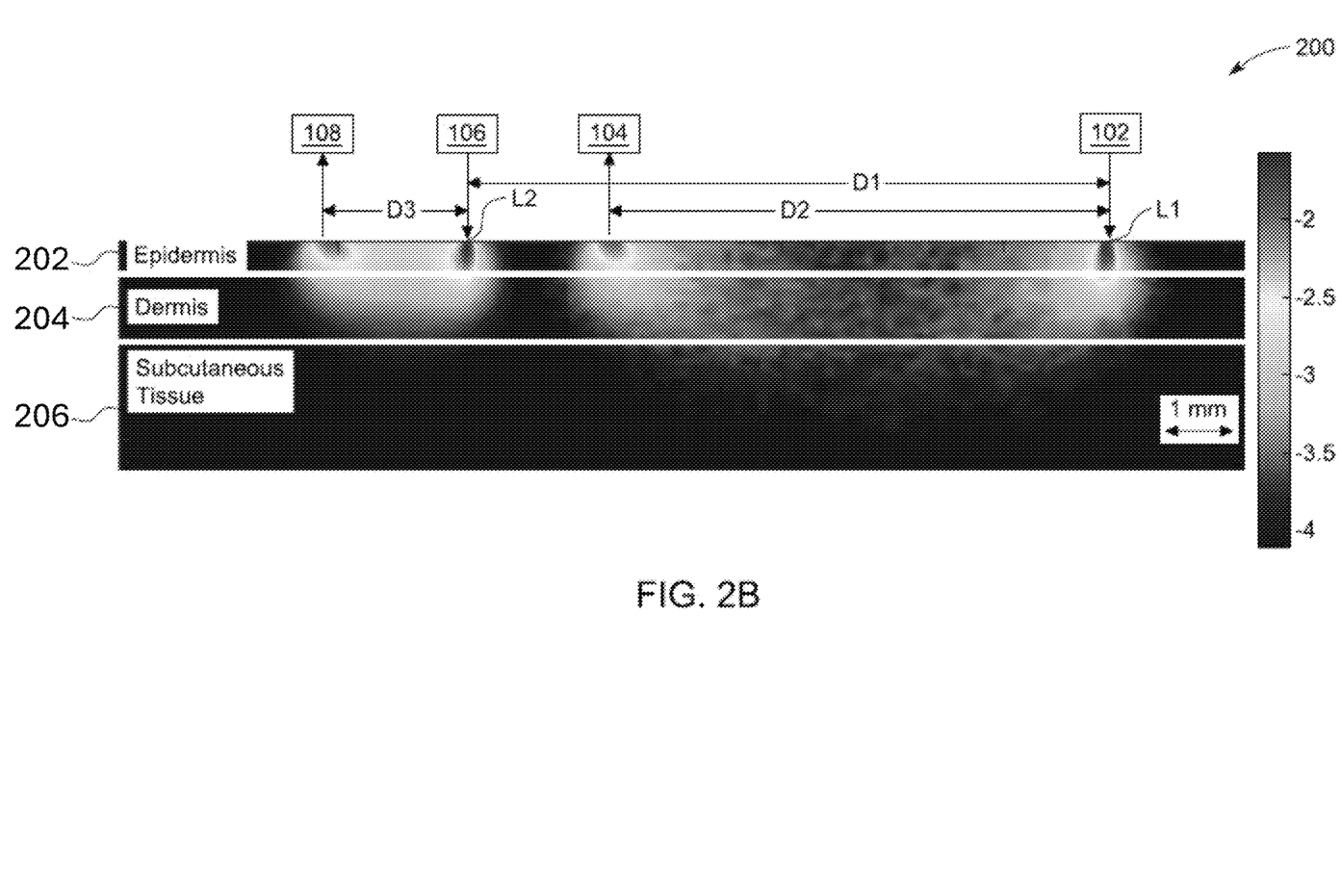
FIG. 2B is a Monte Carlo Simulation (MCS) showing the non-invasive glucose sensor of FIG. 1 in contact with the skin of the subject, according to certain embodiments.

Referring to FIG. 2A, a schematic representation of the non-invasive glucose sensor 100 in contact with the skin 200 of the subject is illustrated. FIG. 2B illustrates a Monte Carlo Simulation (MCS) of FIG. 2A. The skin 200 contains three layers such as an epidermis 202, otherwise referred to as 'the external epidermis 202', a dermis 204 and a subcutaneous tissue 206. The epidermis 202 (the outermost layer of the skin 200) may have a thickness in a range of 0.05 millimeter (mm) to 0.3 mm. The epidermis 202 includes stratum corneum which consists of dead cells. The dermis 204 (middle layer of the skin 200) may have a thickness of up to 1 millimeter (mm). The dermis 204 may include connective tissue, blood vessels, oil and sweat glands, nerves, hair follicles, and other structures. Capillaries present inside the dermis 204 of the skin 200 include glucose. The subcutaneous tissue 206 (inner layer) may have a thickness in a range of 1.65-25.20 mm.

Referring to FIGS. 1-2B, the long channel source 102 excites at a first location 'L1' of the skin 200 of the subject with a first near-infrared (NIR) energy. The long channel detector 104 detects NIR energy emitted from the first location 'L1' of the skin 200 upon excitation of the first NIR energy. The long channel source guide 116 directs the first NIR energy to the first location 'L1' of the skin 200 of the subject, and the long channel detector guide 118 directs the NIR energy emitted from the first location 'L1' of the skin 200 upon excitation of the first NIR energy to the long channel detector 104. The MR energy emitted from the first location 'L1' of the skin 200 may have lower intensity than the first NIR energy. The long channel processor 110 processes a long channel electrical signal 'S1' produced by the long channel detector 104 into a glucose spectroscopic data 'T1'.

The glucose spectroscopic data 'T1' obtained by the method disclosed herein has a dermis sensitivity of at least 30%. In preferred embodiments, the glucose spectroscopic data 'T1' has a dermis sensitivity of about 40%, preferably about 45%, preferably about 50%, preferably about 55%, preferably about 60%. In some embodiment, at least a portion of the first NIR energy is also scattered into the epidermis 202 and the subcutaneous tissue 206.

The first NIR energy of the long channel source may have a wavelength of 1700-1800 nm, preferably 1710-1790 nm, preferably 1720-1780 nm, preferably 1730-1770 nm, preferably 1740-1760 nm, preferably 1745-1755 nm. Most preferably, the first NIR energy has a wavelength of about 1750 nm.

The short channel source 106 excites a second location 'L2' of the skin 200 of the subject with a second NIR energy. The short channel detector 108 detects NIR energy emitted from the second location 'L2' of the skin 200 upon excitation of the second NIR energy. The short channel source guide 120 directs the second NIR energy to the second location 'L2' of the skin 200 of the subject, and the short channel detector guide 122 directs the NIR energy emitted from the second location 'L2' of the skin 200 upon excitation of the second NIR energy to the short channel detector 108. Intensity of the NIR energy emitted from the second location 'L2' of the skin 200 may be lower than that of the second NIR energy exciting the second location 'L2'.

The second NIR energy the short channel source may have a wavelength of 1400-1500 nm, preferably 1410-1490 nm, preferably 1420-1480 nm, preferably 1430-1470 nm, preferably 1440-1460 nm, preferably 1445-1455 nm. Most preferably, the second NIR energy has a wavelength of about 1450 nm.

The short channel processor 112 processes a short channel electrical signal 'S2' produced by the short channel detector 108 into a background spectroscopic data 'T2'. The background spectroscopic data 'T2' obtained by the method disclosed herein has an epidermis sensitivity of at least 15%. In preferred embodiments, the background spectroscopic data 'T2' has an epidermis sensitivity of about 20%, preferably about 30%, preferably about 35%, preferably about 40%, preferably about 45%. In some embodiments, at least a portion of the second NIR energy confined in the epidermis 202 is scattered into the dermis 204.

The first and the second locations 'L1', 'L2' of the skin 200 are each adjacent to the external epidermis 202 of the skin 200. In some embodiments, a distance 'D1' between the first and the second locations 'L1', 'L2' of the skin 200 is in a range of about 7-13 mm, about 7.5-12.5 mm, about 8-12 mm, about 8.5-11.5 mm, about 9-11 mm, about 9.5-10.5 mm, or about 10 mm. In preferred embodiments, a distance 'D1' between the first and the second locations 'L1', 'L2' of the skin 200 is about 8-12 mm, preferably 8.25-11.75 mm, preferably 8.5-11.5 mm, preferably 8.75-11.25 mm, preferably 9-11 mm, preferably 9.25-10.75 mm, preferably 9.5-10.5 mm, preferably 9.75-10.25 mm, preferably 9.9-10.1 mm, or about 10 mm. Alternatively, the first and the second locations 'L1', 'L2' of the skin 200 may be the same.

The skin 200 is located on hands, forearms, forehead, face, fingers, and/or earlobes of the subject. In some embodiments, the skin 200 may also be located on other parts of the body of a human including, but not limited to, legs, feet, and chest.

The depth of light propagation may depend on the distances between the long channel and short channel sources 102, 106 and the long channel and short channel detectors 104, 108. A higher penetration depth of light causes a greater DS.

In preferred embodiments, a source-detector distance 'D2' between the long channel source 102 and the long channel detector 104 is from 5 to 7 mm, preferably from 5.2 to 6.8 mm, preferably from 5.4 to 6.6 mm, preferably from 5.6 to 6.4 mm, preferably from 5.8 to 6.2 mm, preferably from 5.9 to 6.1 mm. Most preferably, the source-detector distance 'D2' between the long channel source 102 and the long channel detector 104 is about 6 mm.

A source-detector distance 'D2' between the long channel source 102 and the long channel detector 104 that is less than 5 mm or greater than 7 mm may decrease the Signal-to-Noise ratio (SNR). As used herein, a SNR is the ratio of intensity of an information carrying electrical signal to that of an interference noise signal. The interference noise signal may refer to the second channel electrical signal 'S2'. The SNR may further refer to the ratio of the first channel electrical signal 'S1' to the second channel electrical signal 'S2'.

In preferred embodiments, a source-detector distance 'D3' between the short channel source 106 and the short channel detector 108 is from 1 to 3 mm, preferably from 1.2 to 2.8 mm, preferably from 1.4 to 2.6 mm, preferably from 1.6 to 2.4 mm, preferably from 1.8 to 2.2 mm, preferably from 1.9 to 2.1 mm. Most preferably, the source-detector distance 'D3' between the short channel source 106 and the short channel detector 108 is about 2 mm.

When the source-detector distance 'D3' is smaller than 3 mm, the light interacts with superficial layer such as the epidermis 202. Such a source-detector distance 'D3' between the short channel source 106 and the short channel detector 108 may cause minimal interference with the dermis 204 of the skin 200 which further helps to obtain the long channel electrical signal 'S1' with the desired signal quality. The source-detector distances 'D2', 'D3' may be otherwise referred to as the Source Detector Separations (SDSs).

The spectroscopic processor 114 subtracts the background spectroscopic data 'T2' from the glucose spectroscopic data 'T1', thereby producing data 'T3' indicative of a quantity of glucose present in the subject's blood. The background spectroscopic data 'T2' may be removed using well-developed algorithms [Neuroimage, 2014, 85, 127-135, incorporated by reference herein in its entirety]; [Neuroimage, 2011, 56, 3, incorporated by reference herein in its entirety]; [Neuroimage, 2012, 59, 3, incorporated by reference herein in its entirety]; and [Neuroimage, 2011, 55, 4, incorporated by reference herein in its entirety]. The 'T3' data indicative of the quantity of glucose present in the subject's blood may be displayed on a display screen 150.

A calibration model may give information either in mathematical numbers or by representing words like low 'sugar', 'mediate sugar', and 'high sugar'. The calibration model may include some emojis such as sad, happy, and crying icons further representing low sugar, 'mediate sugar', and 'high sugar', respectively. The calibration model may produce voices to make the subject aware about the glucose level. In some embodiments, the calibration model may highlight colors each representing the glucose level.

The disclosure will now be illustrated with working examples, which is intended to illustrate the working of disclosure and not intended to be taken restrictively, or to imply any limitations on the scope of the present disclosure.

Methodology

A Monte Carlo Simulation (MCS) is used to find a relation between a dermis sensitivity (DS) and a Signal-Noise Ratio (SNR). Further, dependency of a Source Detector Separation (SDS) on wavelengths used by the MCS is also considered.

MCSs are computational algorithms used for obtaining numerical results depending upon repeated random sampling. In the MCS, the transport of each photon in the skin 200 is modelled based on a probability distribution of the events, i.e., absorption and scattering. The MCS has been used to simulate the propagation of light in the skin 200 for a wide range of wavelengths from 1200 nm to 1900 nm. The MCS has used optical properties such as an absorption coefficient ($\mu_a$), a scattering coefficient ($\mu_s$), and a refractive index (n). The optical properties the absorption coefficient ($\mu_a$), the scattering coefficient ($\mu_s$), and the refractive index (n) all are wavelength dependent. The absorption coefficient refers to a rate of decrease in the intensity of an electromagnetic radiation (NIR) while passing through a medium such as the skin 200.

The scattering coefficient ($\mu_s$) refers to a fractional rate in the transmission of radiation through a scattering medium (the skin 200) at which a flux density of radiation decreases by scattering in respect to the thickness of the scattering medium traversed. Further, a ratio of the velocity of light in a vacuum to the velocity of light in a medium (such as the skin 200) refers to the refractive index (n). The optical properties used in MCS are taken from references [J. Sel. Topics Quantum Electron, 2003, 9, 2, 322-330, incorporated by reference herein in its entirety] determined based on [J. Biomed. Opt, 2001, 6, 2, 167-176, incorporated by reference herein in its entirety], [Phys. Med. Biol, 1998, 43, 9, 2465, incorporated by reference herein in its entirety]. The optical properties may reflect constituents of skin tissues including glucose.

The present example takes reference from FIGS. 2A-7B, the epidermis 202 and the dermis 204 are 0.3 and 1 mm thick. Further, dimensions of the skin 200 are 16×16×16 millimeter cube (mm$^3$) with a voxel size of 0.1 millimeter (mm). For each MCS run, a distribution is acquired for each of the long and short channel devices 105, 109. The experiment is performed to find the desirable source-detector distances 'D2', 'D3'. Thus, three metrics are considered to categorize the performance of the long and short channel devices 105, 109 at a wide range of wavelengths and for a sweep of SDSs. A DS is computed which describes how sensitive a channel is to dermis contents comparative to the overall sensitivity of the skin 200. The DS is a voxel-wise sum of a photon measurement density function (PMDF) in the dermis 204 divided by the voxel-wise sum of the whole PMDF of the skin 200. The PMDF may refer to photon sampling volumes in NIR transillumination of scattering skin tissues. The PMDF identifies the regions within the skin 200 (the dermis 204) contributing to a signal such as the long channel electrical signal 'S1'. Hence, the DS is given by Equation (1):

$$DS = 100 \times \frac{\sum_{Dermis} PMDF}{\sum_{total} PMDF} \quad (1)$$

Similarly, an ES is computed which describes how sensitive a channel is to epidermis contents comparative to the overall sensitivity of the skin 200. The ES is the voxel-wise sum of the PMDF in the epidermis 202 divided by the voxel-wise sum of the whole PMDF. Hence, the ES is given by Equation (2):

$$ES = 100 \times \frac{\sum_{Epidermis} PMDF}{\sum_{total} PMDF} \quad (2)$$

Figure 3A:
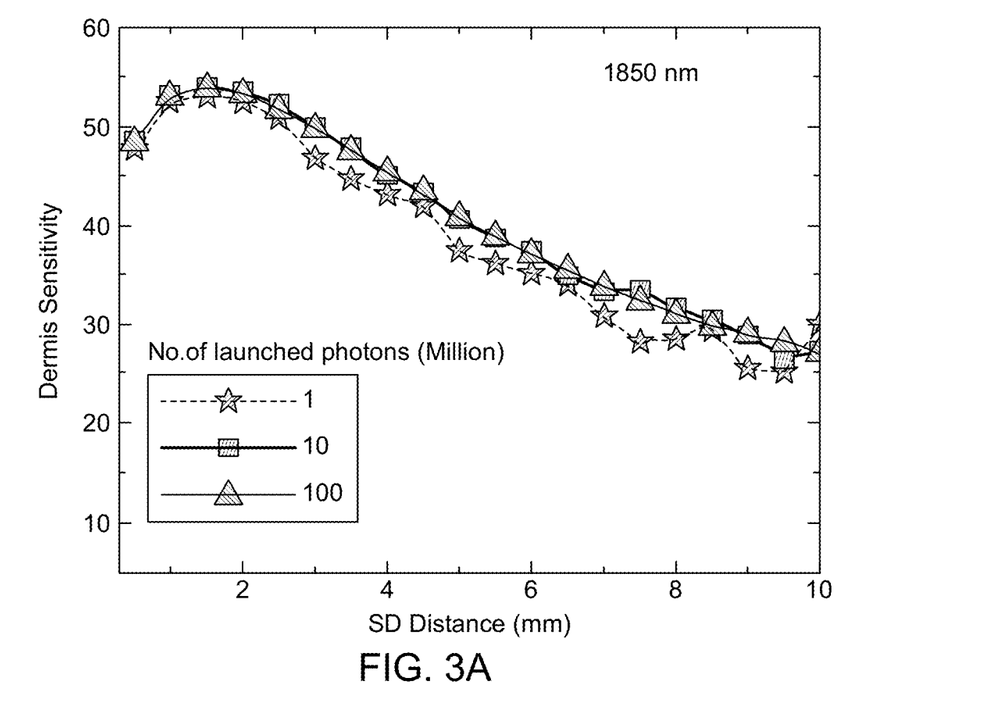
FIG. 3A is a graphical representation of Dermis sensitivities (DS) with respect to Source Detector Separations (SDSs) at 1850 nm.
Figure 3B:
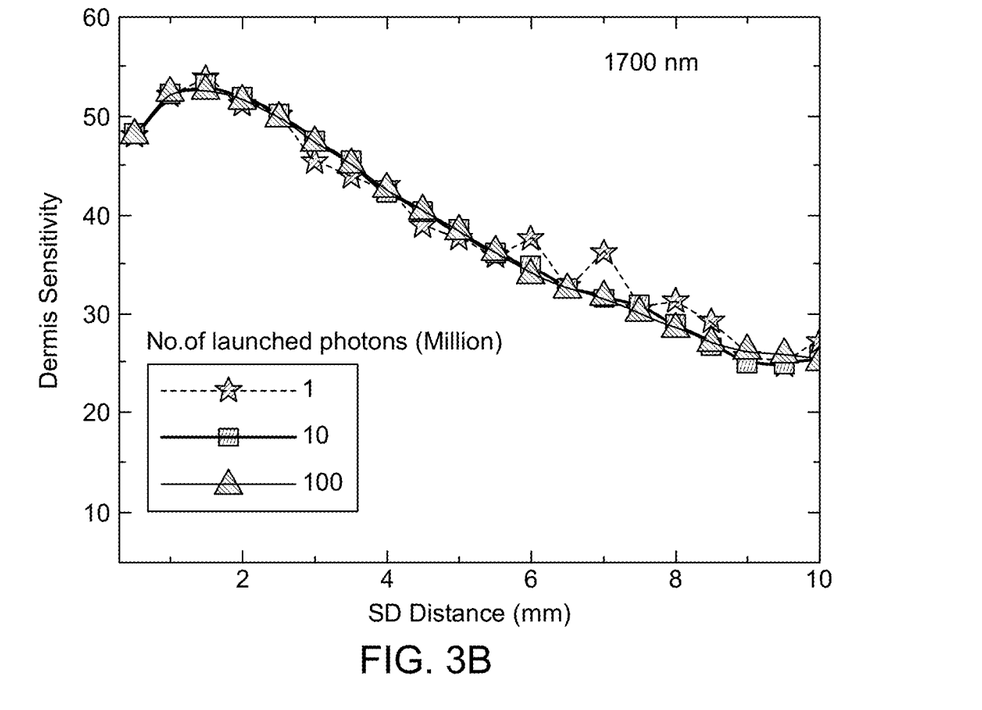
FIG. 3B is a graphical representation of Dermis sensitivities (DS) with respect to SDSs at 1700 nm.
Figure 4A:
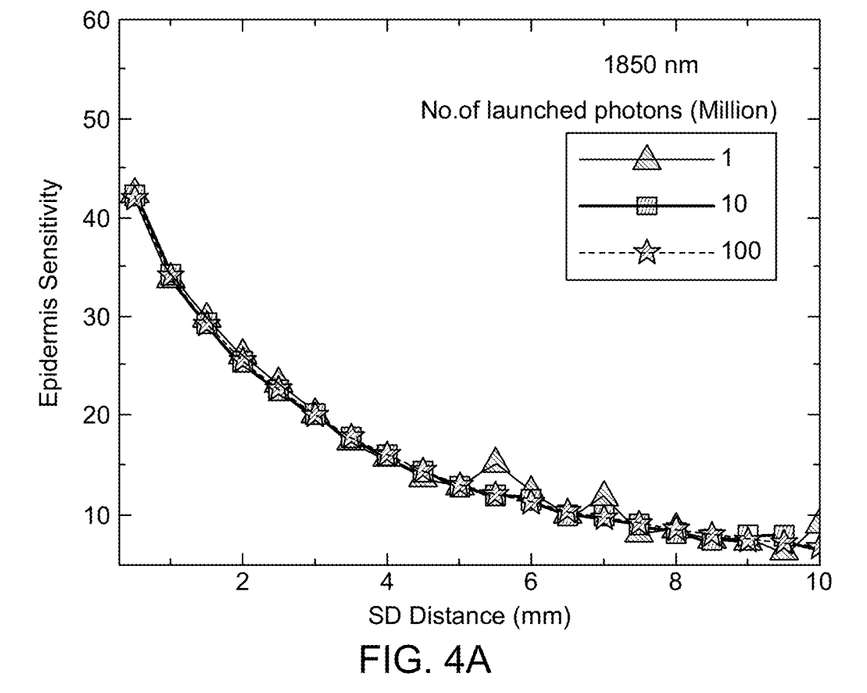
FIG. 4A is a graphical representation of Epidermis sensitivities (ES) with respect to SDSs at 1850 nm.
Figure 4B:
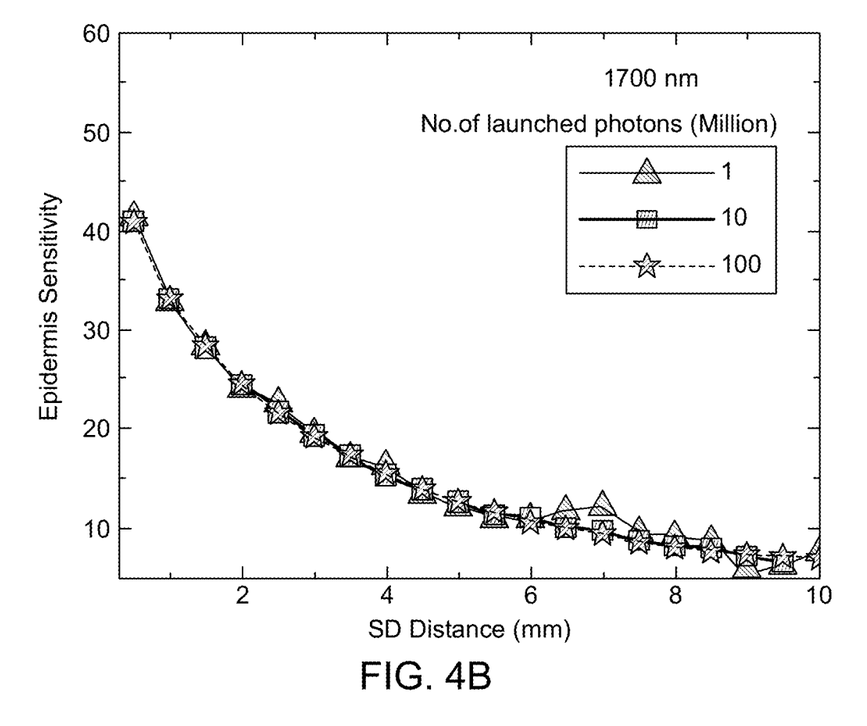
FIG. 4B is a graphical representation of Epidermis sensitivities (ES) with respect to SDSs at 1700 nm.

Referring to FIGS. 3A-4B, dermis and epidermis sensitivities with respect to SDSs are illustrated. The DS and the ES for two wavelengths, 1850 and 1700 nm, versus the SDS for 1 million (M), 10 M, and 100 M photons are considered. A sensitivity value should converge by increasing the photon number. For the long channel devices 105, the convergence may take place with 100 M photons. For the short channel devices 109, the convergence may take place with 10 M photons. The depth of the epidermis 202 is shallower than the dermis 204. Hence, the convergence may take place with a smaller number of photons for the ES compared to the DS. FIGS. 3A-3B show using 100 M photons gives almost the same value as by using 10 M photons. Further, FIGS. 4A-4B show convergence to take place even when the number of photons is just 10 M. The SNR for each SDS is computed to evaluate the response at each wavelength when the SDS increases from 0.5 mm to 10 mm with a step of 0.5 mm. According to [*J. Biomed. Opt*, 2018, 23, 12, incorporated by reference herein in its entirety], the SNR can be computed by running multiple (N=15 and N=30) independently seeded MCSs to obtain a mean (μ) and a standard deviation (σ) and finally converting to Decibel (dB) as given by Equation (3):

$$SNR(SD) = 20\log_{10}\frac{\mu(SD)}{\sigma(SD)} \quad (3)$$

Results and Discussion

Figure 5A:
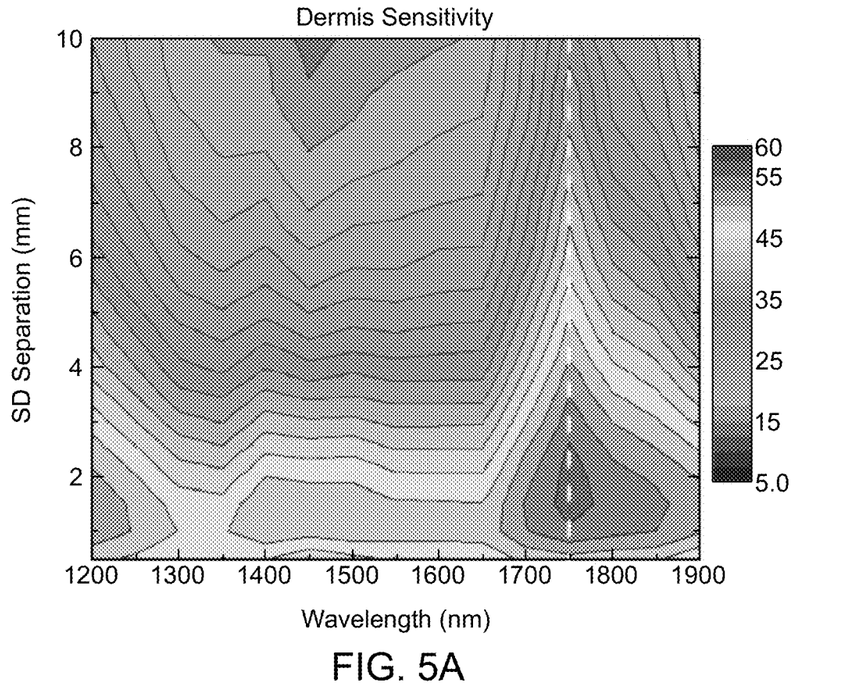
FIG. 5A is a graphical representation of dermis sensitivity portfolios for a range of wavelengths between 1200 nanometer (nm) and 1900 nm.
Figure 5B:
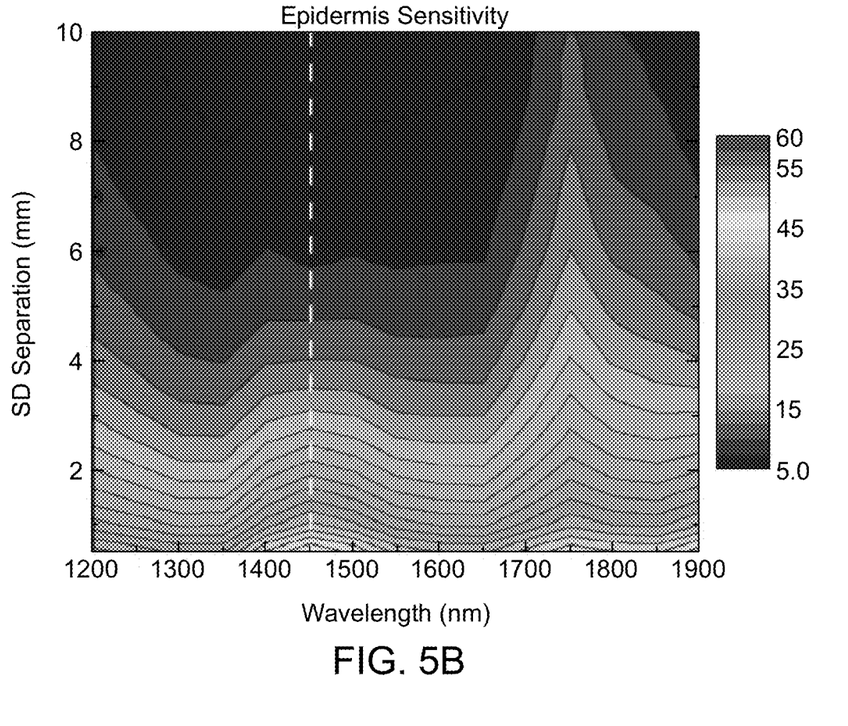
FIG. 5B is a graphical representation of epidermis sensitivity portfolios for a range of wavelengths between 1200 nanometer (nm) and 1900 nm.

Referring to FIGS. 5A-5B, dermis and epidermis sensitivity portfolios for a range of wavelengths between 1200 nm and 1900 nm are illustrated. The ES and the DS are calculated while sweeping SDSs between 0.5 mm to 10 mm with a step size of 0.5 mm and increasing a source wavelength from 1200 nm to 1900 nm with a step of 50 nm. FIG. 5A shows the 1750 nm wavelength features the highest DS for the whole range of the SDSs. Further, FIG. 5B shows a wavelength between 1300 nm and 1650 nm featuring a minimum sensitivity in the dermis 204 and a maximum sensitivity in the epidermis 202. The ES peaks at a 1450 nm wavelength at 0.5 mm and decreases rapidly beyond SDS equals to 3 mm. Therefore, the wavelength 1450 nm for the short channel 109 includes an SDS smaller than 3 mm.

Figure 6A:
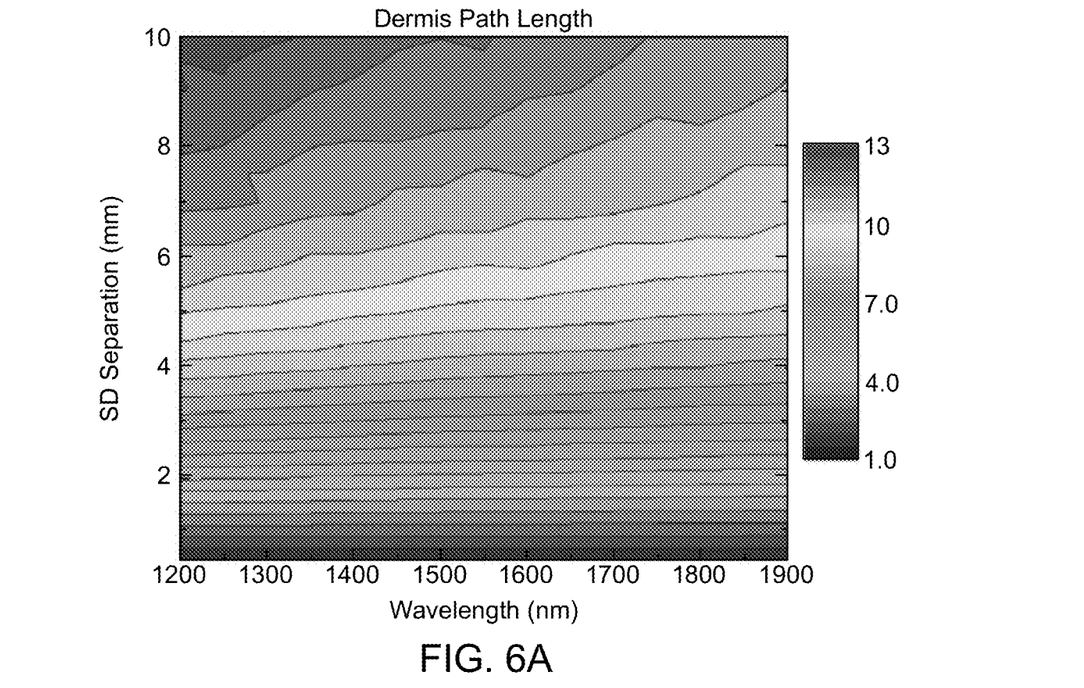
FIG. 6A is a graphical representation of average photon path lengths in a dermis as a function of the SDSs.
Figure 6B:
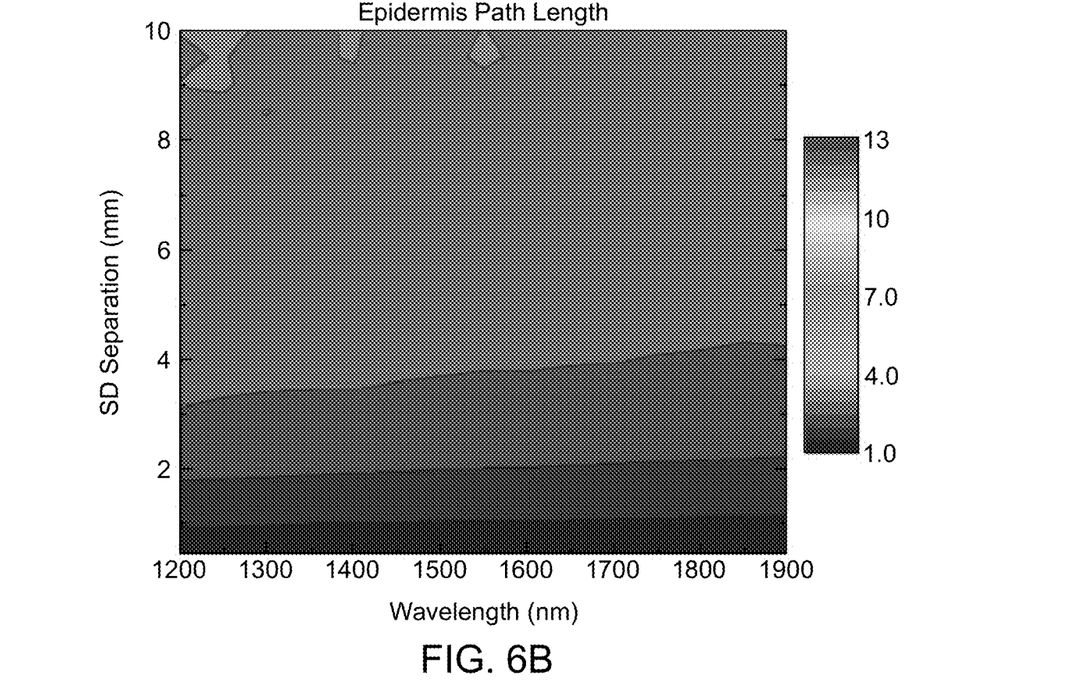
FIG. 6B is a graphical representation of average photon path lengths in the epidermis as a function of the SDSs.

Referring to FIGS. 6A-6B, average photon path lengths in the dermis 204 and epidermis 202 as function of SDSs are illustrated. For the dermis 204, no change in the average photon path length is observed for all wavelengths when the SDS is less than 4 mm. When the SDS is greater than 4 mm, a larger average photon path length for short wavelengths can be observed compared to long wavelengths. In the epidermis 202, no significant changes in the average photon path lengths regardless of the wavelengths are observed. The average photon path length is dependent on a concerned layer of the skin 200. The average photon path length is also dependent on the absorption and scattering coefficients dependent on wavelengths. FIG. 6A shows that the average photon path length interacts with glucose contents in the dermis 204. Also, there is no significant change in the average photon path length for a small change in the wavelength. FIG. 6B shows that average photon path length for the epidermis 202 is about 4 mm or less.

Figure 7A:
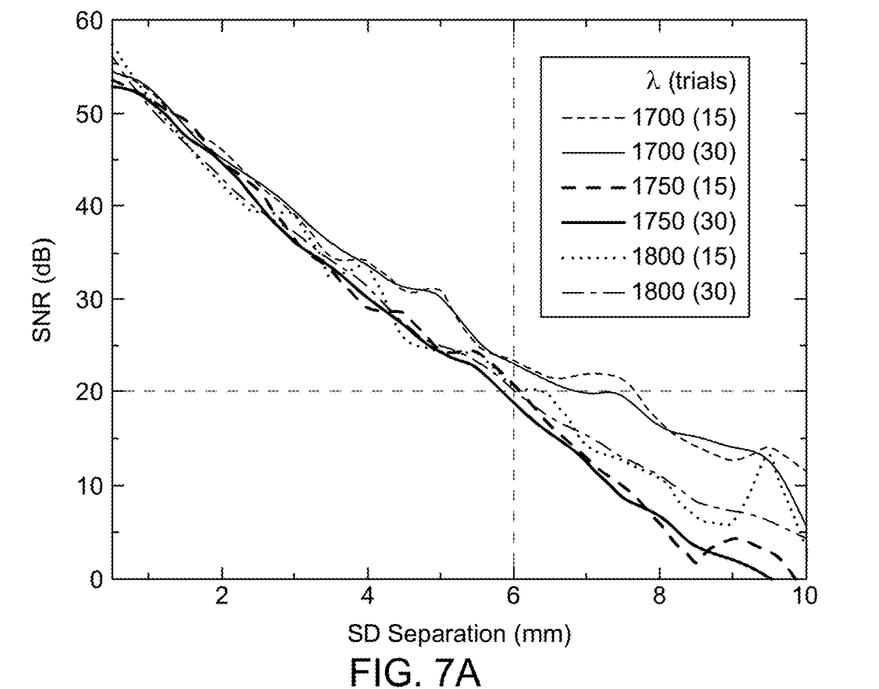
FIG. 7A is a graphical representation of calculated Signal-to-Noise ratios (SNRs) at different SDSs for the long channel at a wavelength ranging from 1700-1800 nm.
Figure 7B:
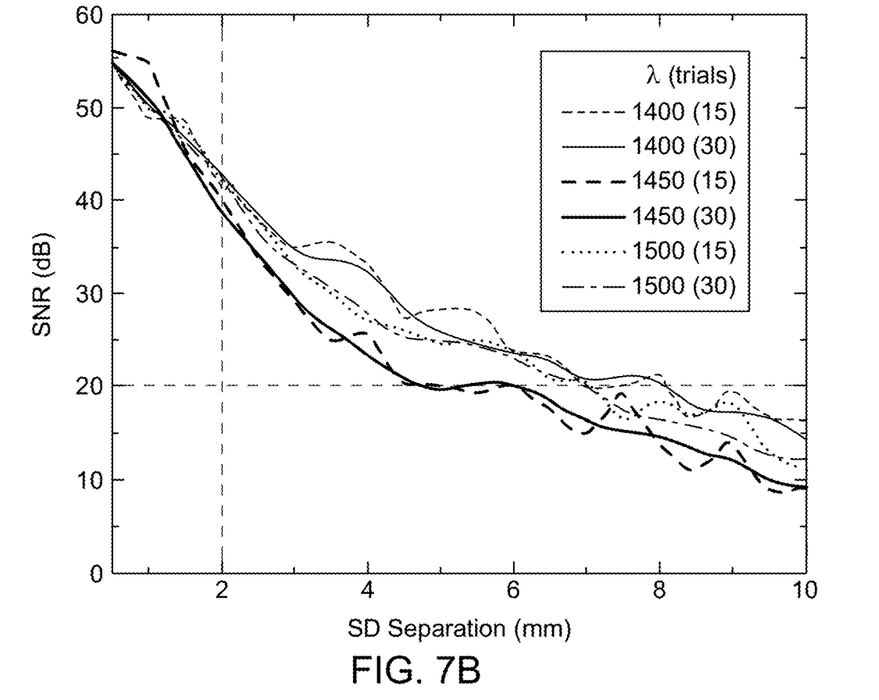
FIG. 7B is a graphical representation of calculated Signal-to-Noise ratios (SNRs) at different SDSs for the short channel at a wavelength ranging from 1400-1500 nm.

Referring to FIGS. 7A-7B, calculated SNRs for different SDSs are illustrated. An SNR can be calculated by running multiple (N=15 and N=30) independently seeded the MCS. The effect of calculating the SNR with the number (N) of independently seeded the MCS is shown by presenting the results of calculating SNR for nominal values of the wavelength 1750 nm and 1450 nm selected from the ES and DS results shown in FIGS. 5A-5B for both N=15 and N=30 as well as ±50 nm with reference to the 1750 nm and 1450 nm. The SNR decreases with increasing the SDS. However, on increasing the independently seeded MCS smoothens the curves. For a wavelength of 1400 nm, the average of the variations between N=15 and N=30 in the SNR is less than 5%. Further, for the wavelength of 1400 nm, the average of the variations between N=15 and N=40 in the SNR is reduced to 2%. Hence, the N=30 is considered. In the present experiment, an SNR of 20 dB is a threshold value and dependent on a DS. In some embodiments, a lower value for the SNR may also be selected.

FIG. 7A shows while the SNR is almost the same for all wavelengths for all the SDSs less than 3 mm, a divergence in the SNR emerges for a separation of 3 mm and beyond. The SNR for the long channel 105 drops below 20 dB for SDSs equal to or more than 6 mm for all wavelengths of 1700, 1750, and 1800 nm. Considering the DS results in FIG. 5A and the SNR in FIG. 7A for the wavelengths for the long channel 105, the 6 mm is the 'D2' for the wavelength 1750 nm. As the DS drops from 43.7 at 1750 nm to 34.1 only at 1700 nm, no difference in the SNR is observed in case of 1700 nm.

FIG. 7B shows while the SNR is almost the same for all wavelengths such as 1400, 1450, and 1500 nm for all SDS less than 2 mm. The ES is better at 1450 nm than at 1400 nm. According to FIG. 5A, the SDS should be 2 mm or larger in order to minimize the DS. Furthermore, according to FIG. 5B, the separation should be as small as possible to obtain the desirable short channel electrical signal 'S2'. Therefore, for the short channel 109, the 2 mm is the 'D3' for the wavelength of 1450 nm.

Figure 9:
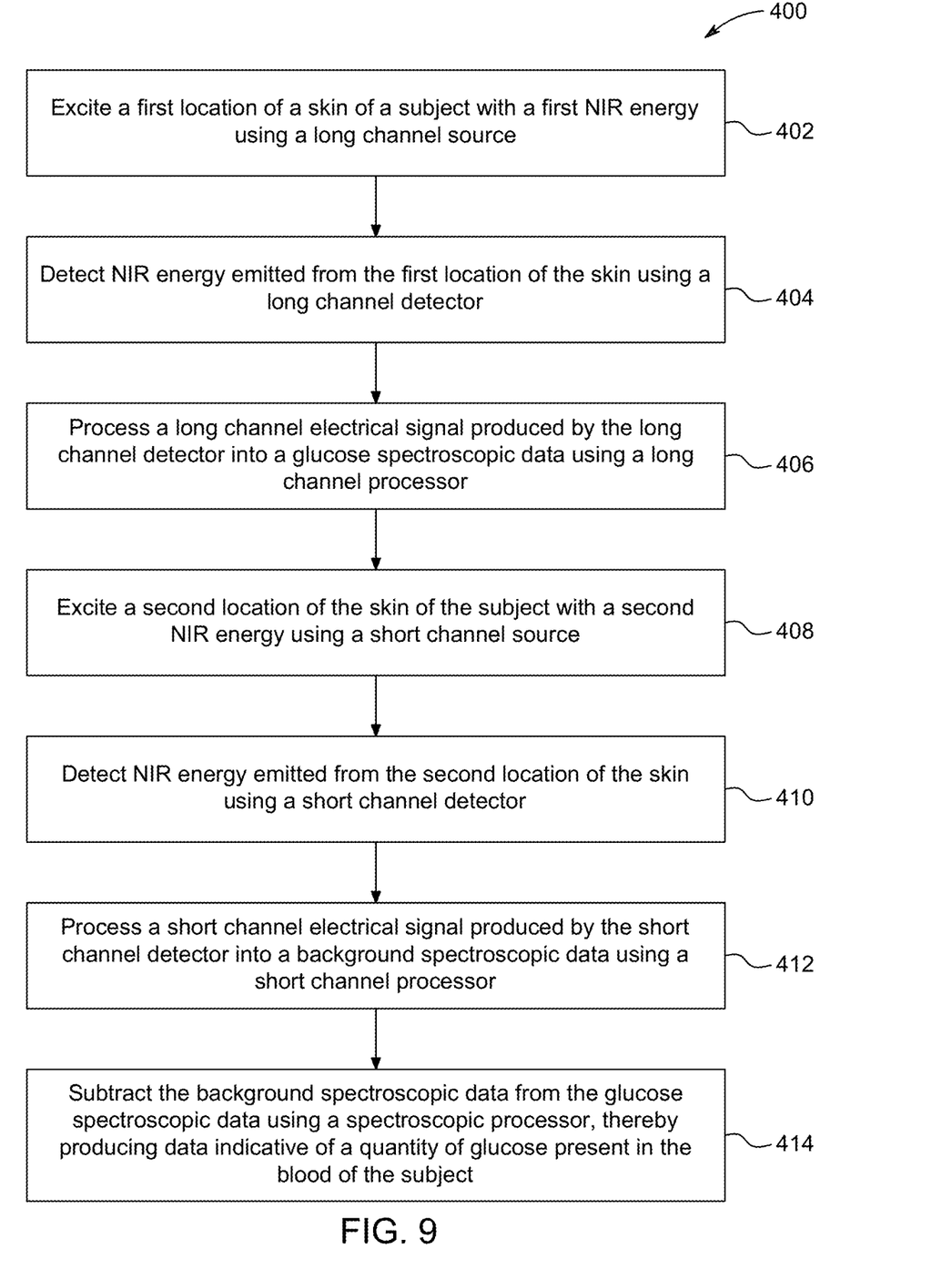
FIG. 9 is a schematic flow diagram of a method of determining glucose level in the subject's blood using the non-invasive glucose sensor of FIG. 1, according to certain embodiments.

Referring to FIG. 9, a schematic flow diagram of a method 400 of determining glucose level in the subject's blood using the non-invasive glucose sensor 100 is illustrated. The method 400 is described with reference to the non-invasive glucose sensor 100 illustrated in FIGS. 1-2B, and FIG. 8. The order in which the method 400 is described is not intended to be construed as a limitation, and any number of the described method steps can be combined in any order to implement the method 400. Additionally, individual steps may be removed or skipped from the method 400 without departing from the spirit and scope of the present disclosure. In an embodiment, the method 400 may be executed by the non-invasive glucose sensor 100 of the present disclosure.

At step 402, the method 400 includes exciting the first location 'L1' of the skin 200 of the subject with the first NIR energy using the long channel source 102. The first NIR energy has the wavelength of about 1750 nm. The long channel source 102 may directly or indirectly touch the skin 200 of the subject. As soon the wearable electronic device 300 is activated, the long channel source 102 starts exciting the first location 'L1' of the skin 200. The excitement of the first location 'L1' of the skin 200 may not cause any vibrations to the skin 200. The first NIR energy may not be felt by the skin 200. The first NIR energy may excite the glucose content of the dermis 204.

At step 404, the method 400 includes detecting NIR energy emitted from the first location 'L1' of the skin 200 using the long channel detector 104. The source-detector distance 'D2' between the long channel source 102 and the long channel detector 104 is about 6 mm. At least a part of the first NIR energy is absorbed by the glucose content present in the dermis 204 of the skin 200. Rest of the first NIR energy is detected as the NIR energy by the long channel detector 104.

At step 406, the method 400 includes processing the long channel electrical signal 'S1', produced by the long channel detector 104 into the glucose spectroscopic data 'T1' using the long channel processor 110. The glucose spectroscopic data 'T1' has the dermis sensitivity (DS) of about 40%.

At step 408, the method 400 includes exciting the second location 'L2' of the skin 200 of the subject with the second NIR energy using the short channel source 106. The second NIR energy has the wavelength of about 1450 nm. The second NIR energy excites different constituents of the epidermis 202 such as the melanin and Deoxyribonucleic acid (DNA).

At step 410, the method 400 includes detecting NIR energy emitted from the second location 'L2' of the skin 200 using the short channel detector 108. The source-detector distance 'D3' between the short channel source 106 and the short channel detector 108 is about 2 mm.

The short channel detector 108 detects the NIR energy emitted by the constituents of the epidermis 202 as most of the second NIR energy is absorbed by the constituents of the epidermis 202.

At step 412, the method 400 includes processing the short channel electrical signal 'S2' produced by the short channel detector 108 into the background spectroscopic data 'T2' using the short channel processor 112. The background spectroscopic data 'T2' has the epidermis sensitivity of about 30%.

At step 414, the method 400 includes subtracting the background spectroscopic data 'T2' from the glucose spectroscopic data 'T1' using the spectroscopic processor 114, thereby producing the data 'T3' indicative of the quantity of glucose present in the subject's blood. Further, the quantity of glucose is determined using absorption signals ranging from 1200 nm to 1900 nm of the data 'T3' produced by subtracting the background spectroscopic data 'T2' from the glucose spectroscopic data 'T1' using the spectroscopic processor 114.

Obviously, numerous modifications and variations of the present disclosure are possible in light of the above described techniques. It is therefore to be understood that within the scope of the appended claims, the invention may be practiced otherwise than as specifically described herein.

The invention claimed is:

1. A non-invasive glucose sensor for a subject, comprising:
    a long channel source that is configured to excite a first location of a skin of the subject with a first near-infrared (NIR) energy;
    a long channel detector that is configured to detect NIR energy emitted from the first location of the skin upon excitation of the first NIR energy;
    a short channel source that is configured to excite a second location of the skin of the subject with a second NIR energy having a second wavelength that is shorter than a first wavelength of the first NIR energy;
    a short channel detector that is configured to detect NIR energy emitted from the second location of the skin upon excitation of the second NIR energy;
    a long channel processor that processes a long channel electrical signal produced by the long channel detector into a glucose spectroscopic data;
    a short channel processor that processes a short channel electrical signal produced by the short channel detector into a background spectroscopic data; and
    a spectroscopic processor that subtracts the background spectroscopic data from the glucose spectroscopic data, thereby producing data indicative of a quantity of glucose present in blood of the subject,
    wherein the first and the second locations of the skin are each adjacent to an external epidermis of the skin,
    the first wavelength of the first NIR energy is 1750 nanometers (nm) and the second wavelength of the second NIR energy is 1450 nm,
    the long channel source, the long channel detector, the short channel source, and the short channel detector are positioned exclusively along a shared axis, and
    a first source-detector distance between the long channel source and the long channel detector along the shared axis is from 5 to 7 millimeters (mm) and a second source-detector distance between the short channel source and the short channel detector along the shared axis is from 1 to 3 mm.

2. The non-invasive glucose sensor of claim 1, wherein the first source-detector distance between the long channel source and the long channel detector is about 6 mm.

3. The non-invasive glucose sensor of claim 1, wherein the second source-detector distance between the short channel source and the short channel detector is about 2 mm.

4. The non-invasive glucose sensor of claim 1, further comprising a long channel source guide that directs the first NIR energy to the first location of the skin of the subject, and a long channel detector guide that directs the NIR energy emitted from the first location of the skin upon excitation of the first NIR energy to the long channel detector.

5. The non-invasive glucose sensor of claim 4, further comprising a short channel source guide that directs the second NIR energy to the second location of the skin of the subject, and a short channel detector guide that directs the NIR energy emitted from the second location of the skin upon excitation of the second NIR energy to the short channel detector.

6. The non-invasive glucose sensor of claim 5, wherein the long channel source guide, the long channel detector guide, the short channel source guide, and the short channel detector guide each independently comprises at least one optical fiber.

7. The non-invasive glucose sensor of claim 1, wherein the long channel source and the short channel source each independently comprises at least one light source that emits 1 million to 100 million photons.

8. The non-invasive glucose sensor of claim 1, wherein the long channel detector and the short channel detector each independently comprises at least one photodiode.

9. The non-invasive glucose sensor of claim 1, wherein a distance between the first and the second locations of the skin is about 8-12 mm.

10. A wearable electronic device, comprising:
    the non-invasive glucose sensor of claim 1; and
    a control unit configured to control the non-invasive glucose sensor.

11. The wearable electronic device of claim 10, further comprising a first support band having a first opening and a second opening, the second opening being larger than the first opening, and a second support band connected to the first support band and having a hook and loop fastener.

12. The wearable electronic device of claim 11, further comprising a display screen attached to an outer surface of the first support band or the second support band.

13. A method of determining glucose level in the blood of the subject using the non-invasive glucose sensor of claim 1, the method comprising:
    exciting the first location of the skin of the subject with the first NIR energy using the long channel source;
    detecting NIR energy emitted from the first location of the skin using the long channel detector;
    processing the long channel electrical signal produced by the long channel detector into the glucose spectroscopic data using the long channel processor;
    exciting the second location of the skin of the subject with the second NIR energy using the short channel source;
    detecting NIR energy emitted from the second location of the skin using the short channel detector;

processing the short channel electrical signal produced by the short channel detector into the background spectroscopic data using the short channel processor; and subtracting the background spectroscopic data from the glucose spectroscopic data using the spectroscopic processor, thereby producing data indicative of a quantity of glucose present in the blood of the subject.

14. The method of claim 13, wherein a source-detector distance between the long channel source and the long channel detector is about 6 mm, and a source-detector distance between the short channel source and the short channel detector is about 2 mm.

15. The method of claim 14, wherein the glucose spectroscopic data has a dermis sensitivity of about 40%, and the background spectroscopic data has an epidermis sensitivity of about 30%.

16. The non-invasive glucose sensor of claim 1, wherein the long channel source and the long channel detector are configured to operate in a first period and the short channel source and the short channel detector are configured to operate in a second period that is offset in time from the first period.

* * * * *